(12) United States Patent
Chin et al.

(10) Patent No.: US 8,540,896 B2
(45) Date of Patent: *Sep. 24, 2013

(54) CHIRAL COMPOUND AND LIQUID CRYSTAL COMPOSITION CONTAINING THE SAME

(75) Inventors: Chih-Lung Chin, Taoyuan County (TW); Hui-Fang Tseng, Fengyuan (TW); Wan-Chi Chen, Taoyuan County (TW); Chun-Ming Wu, Banqiao (TW); Kung-Lung Cheng, Hsinchu (TW)

(73) Assignee: Industrial Technology Research Institute, Hsinchu County (TW)

( * ) Notice: Subject to any disclaimer, the term of this patent is extended or adjusted under 35 U.S.C. 154(b) by 453 days.

This patent is subject to a terminal disclaimer.

(21) Appl. No.: 12/906,952

(22) Filed: Oct. 18, 2010

(65) Prior Publication Data

US 2011/0109868 A1    May 12, 2011

(30) Foreign Application Priority Data

Nov. 12, 2009  (TW) ................................ 98138370 A (51) Int. Cl.
*C09K 19/54* (2006.01)
*C09K 19/52* (2006.01)
*C07D 493/04* (2006.01)

(52) U.S. Cl.
USPC .................... 252/299.5; 252/299.01; 549/464

(58) Field of Classification Search
USPC ............................ 252/299.01, 299.5; 549/464
See application file for complete search history.

(56) References Cited

U.S. PATENT DOCUMENTS

| | | | |
|---|---|---|---|
| 6,589,445 B2 | 7/2003 | Sugiyama et al. | |
| 6,610,216 B2 | 8/2003 | Yumoto et al. | |
| 6,879,362 B2 | 4/2005 | Kawabata | |
| 7,022,259 B2 | 4/2006 | Lee et al. | |
| 7,122,227 B2 | 10/2006 | Vaughn-Spickers et al. | |
| 7,294,369 B2 | 11/2007 | Harding et al. | |
| 7,311,948 B2 * | 12/2007 | Lub et al. ................. | 428/1.1 |
| 7,425,356 B2 | 9/2008 | Taugerbeck et al. | |
| 7,452,482 B2 | 11/2008 | Welter | |
| 8,383,008 B2 * | 2/2013 | Tseng et al. ............. | 252/299.61 |
| 2002/0076510 A1 | 6/2002 | Farrand | |

FOREIGN PATENT DOCUMENTS

| | | |
|---|---|---|
| EP | 1273585 A1 | 1/2003 |
| JP | 2006162814 A | 6/2006 |
| TW | I225090 | 12/2004 |
| TW | I238186 | 8/2005 |
| TW | I250200 | 3/2006 |
| TW | 95146449 | 12/2006 |
| TW | I297355 | 6/2008 |
| TW | 200838991 | 10/2008 |
| WO | 2004087835 A1 | 10/2004 |

OTHER PUBLICATIONS

Schwarz et al., "New Polymer Synthesis. LXXXIII. Synthesis of Chiral and Cholesteric Polyesters from Silylated 'Sugar Diols'", Journal of Polymer Science: Part A: Polymer Chemistry, vol. 34, 603-611 (1996).

Vill et al., "Molekulares Verdrillungsvermögen von Kohlenhydrat-Derivaten", Z. Naturforsch., 43a, 1119-1125 (1988).

First examination opinion notification issued by the China Intellectual Property Office on Feb. 15, 2012, for the above-referenced application's counterpart application in China (Application No. 200910253431.8).

Lub et al., "Photoisomerizable chiral compounds derived from isosorbide and cinnamic acid", Liquid Crystals, vol. 32, No. 8, pp. 1031-1044 (Aug. 2005).

Lub et al., "Synthesis and properties of photoisomerizable derivatives of isosorbide and their use in cholesteric filters", Advanced Functional Materials, vol. 15, No. 12, pp. 1961-1972 (2005).

\* cited by examiner

*Primary Examiner* — Shean C Wu
(74) *Attorney, Agent, or Firm* — Pai Patent & Trademark Law Firm; Chao-Chang David Pai (57) ABSTRACT

A chiral compound of formula (I) or (II) is provided, wherein each of $R_1$ and $R_2$ independently, is hydrogen, hydroxyl, halogen, amino, nitrile, $C_{1-10}$ alkyl, or $C_{1-10}$ alkoxyl. A liquid crystal composition comprising 80-99.5 parts by weight of a liquid crystal host; and 0.5-20 parts by weight of the chiral compound as described above is also provided.

21 Claims, 2 Drawing Sheets

CHIRAL COMPOUND AND LIQUID CRYSTAL COMPOSITION CONTAINING THE SAME

CROSS REFERENCE TO RELATED APPLICATIONS

This Application claims priority of Taiwan Patent Application No. 098138370, filed on Nov. 12, 2009, the entirety of which is incorporated by reference herein.

BACKGROUND OF THE INVENTION

1. Field of the Invention

The present invention relates to a chiral compound, and in particular relates to a photosensitive chiral compound having high helical twisting power and a liquid crystal composition containing the same.

2. Description of the Related Art

A cholesteric liquid crystal display can reflect environmental light without requiring a backlight module and a polarizer film, and therefore can provide reduced power consumption when compared with the conventional transmissive liquid crystal displays. Since the cholestric liquid crystal display can reflect lights of various wavelengths, color images can be displayed without a color filter.

A cholesteric liquid crystal, also called a chiral nematic liquid crystal material, is composed of a nematic liquid crystal and chiral dopant. The nematic liquid crystal exhibits higher helical twisting power than that of twisted nematic (TN) or super twisted nematic (STN) liquid crystals due to the presence of the chiral dopant.

The pitch (p) of the cholesteric liquid crystal is determined by the concentration (c) and the helical twisting power (HTP) of the chiral dopant, which can be expressed by the formula:

$$p=1/(\text{HTP} \cdot c)$$

The reflected wavelength of the cholesteric liquid crystal is determined by the pitch thereof, while the pitch is controlled by the helical twisting power and the concentration of the chiral dopant. Therefore, under a given value of pitch, the higher the helical twisting power, the lower the required concentration of the chiral dopant. If the chiral dopant has poor solubility in the liquid crystal host (multi-layer nematic liquid crystal), it will be difficult to tailor the liquid crystal formulation.

It is desirable to use a photosensitive chiral compound having high helical twisting power in optical writing cholesteric liquid crystal displays. The conformation of the chiral molecules in the liquid crystal can be altered by illumination to result in the change of the helical twisting power, which in turn, changes the pitch of the cholestric liquid crystal to obtain a different color of reflected light. However, if the chiral compound has a inherent color (such as an orange azo molecule), its addition to the liquid crystal host will interfere with color reflection, making the chiral compound not suitable for use as the liquid crystal formulation in an optical writing cholestric liquid crystal device.

Accordingly, it is desirable to provide photosensitive chiral compounds having high helical twisting power, good solubility in a liquid crystal formulation, and colorless properties, to be used in an optical writing cholestric liquid crystal device. Furthermore, the liquid crystal composition preferably should have high color purity and stable temperature dependence.

BRIEF SUMMARY OF THE INVENTION

The invention provides a chiral compound, having a general formula of formula (I) or (II)

$R_1$ and $R_2$ are independently hydrogen, hydroxyl, halogen, amino, nitro, nitrile, $C_{1-10}$ alkyl, $C_{1-10}$ alkoxyl, aryl, heteroaryl, cycloalkyl, or hetero cycloalkyl.

The invention further provides a liquid crystal composition, comprising: 80-99.5 parts by weight of a liquid crystal host; and 0.5-20 parts by weight of the chiral compound described above, and preferably 3-10 parts by weight of the chiral compound described above.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Manufacturing of an optical writing cholesteric liquid crystal display requires an photosensitive chiral compound having high helical twisting power. The photosensitive chiral compound should be colorless to avoid interference with the wavelengths of the reflective light. To this end, asymmetric derivatives of chiral molecules 1,4:3,6-isomannide and isosorbide are employed (as shown below). A cholestric liquid crystal phase can be readily obtained by adding a small amount of the above chiral molecule in a nematic liquid crystal due to the high helical power of the molecule. In addition, acrylic functionality is provided in the molecule for a photosensitive function.

Isomannide      Isosorbide

The chiral compound of the invention has a general formula of formula (I) or (II):

$R_1$ and $R_2$ are independently hydrogen, hydroxyl, halogen, amino, nitro, nitrile, $C_{1-10}$ alkyl, $C_{1-10}$ alkoxyl, aryl, heteroaryl, cycloalkyl, or hetero cycloalkyl, wherein $C_{1-10}$ alkyl and $C_{1-10}$ alkoxyl can be a straight chain or branched chain. In one embodiment, $R_1$ and $R_2$ are independently hydrogen, $C_{1-10}$ alkyl, or $C_{1-10}$ alkoxyl. In another embodiment, $R_1$ and $R_2$ are both alkoxyl.

In the above, the term "aryl" represents a mono or polycyclic carbocyclic ring system with one or more aromatic rings. For example, phenyl, tolyl, naphthyl, tetrahydronaphthyl, biphenyl, phenanthryl, anthracyl, or the like.

The term "heteroaryl" represents an aryl group with one or more hetero atoms (such as nitrogen, oxygen, sulfur). For example, pyridyl, furyl, thienyl, imidazolyl, or the like.

The term "cycloalkyl" represents a non-aromatic, moco or polycyclic carbocyclic ring compound having 3-12 ring carbons. For example, cyclopropyl, cyclobutyl, cyclopentyl, cyclohexyl, cyclooctyl, dicyclo[2,2,1]-octyl, or the like.

The term "heterocyclic" represents a cycloalkyl with one or more hetero atoms (such as nitrogen, oxygen, sulfur). For example, 1,3-dioxolane, pyrrolidinyl, pyrazolinyl, piperidinyl, piperazinyl, tetrahydrofuryl, or the like.

Moreover, the aryl, heteroaryl, cycloalkyl, or heterocycloalkyl may have one or more hydrogens which are further substituted by halogen, hydroxyl, amino, or other functional groups.

As shown in formulas (I) and (II), the chiral compound of the invention is an asymmetrical isomannide/isosorbide chiral compound with a photosensitive functional group. As compared to the conventional compound having two photosensitive functional groups (such as those disclosed in U.S. Pat. No. 6,589,445), the chiral compound with a single photosensitive group can improve color purity of the cholestric liquid crystal.

The chiral compound of formula (I) can be formed from isomannide after two steps of esterifications. The reaction is shown as follows (wherein $R_1$ and $R_2$ have the meaning described above; X represents —OH or —Cl):

Similarly, the chiral compound of formula (II) can be formed from isosorbide after two steps of esterifications. The reaction is shown as follows (wherein $R_1$ and $R_2$ have the meaning described above; X represents —OH or —Cl):

The first esterification reaction is usually performed under a temperature between 0° C. and room temperature for 4 hours. The second esterification reaction is usually performed under a temperature of 80° C. for 20 hours. Specific steps of the esterifications are described in detail in the following examples.

The chiral compound is in a white solid form, and has good solubility in the nematic liquid crystal formulation. Moreover, the chiral compound is colorless when dissolved, so the color of reflective light is not affected. Furthermore, the chiral compound of the invention usually has a helical twisting power which is larger than 30 $\mu m^{-1}$. Therefore, only a small amount of the chiral compound is needed when used in the liquid crystal composition, such that detrimental effects on optoelectric properties and liquid crystal behavior due to excess amount of the chiral compound can be avoided.

In one embodiment, the liquid composition of the invention comprises:

(a) 80-99.5 parts by weight of a liquid crystal host; and
(b) 0.5-20 parts by weight, or preferably 3-10 parts by weight of the chiral compound of formulas (I) and (II).

In another embodiment, the liquid composition of the invention comprises:

(a) 100 parts by weight of a liquid crystal host; and
(b) 3-20 parts by weight, or preferably 5-15 parts by weight of the chiral compound of formulas (I) and (II).

The chiral compound of the invention can serve as a photosensitive chiral additive for a nematic liquid crystal, smectic liquid crystal, or discotic liquid crystal. Preferably, the chiral compound of the invention can be added into a nematic liquid crystal to provide a cholestric liquid crystal formulation for an optical writing cholestric liquid crystal display.

The liquid crystal host used herein may or may not contain a polymerizable group. Further, the liquid crystal composition may optionally contain polymerizable monomers, polymerized initiators, binder resins, solvents, surfactants, thickening agents, UV-absorbents, or other chiral additives. Reference may be made to U.S. Pat. No. 6,589,445 for description of specific examples of liquid crystal hosts and compositions thereof, which is incorporated herein by reference.

The conformation of the photosensitive chiral compound in the invention can be altered by illumination to change the helical twisting power. As a result, the pitch (p) of the cholestric liquid crystal and therefore the color of the reflective light are changed. Depending on the amount of time for illumination, the liquid crystal composition of the invention may have a shift in the wavelength of 50-250 nm to exhibit specific reflection wavelengths such as red (R), green (G), blue (B), and an invisible light spectrum (380-800 nm). UV is a preferred light source for the above illumination because it has higher energy that can shorten the time required for altering molecular conformations.

Compared to the conventional compound having two photosensitive functional groups, the chiral compound with a single photosensitive functional group of the invention can provide a cholestric liquid crystal formulation with a smaller FWHM (Full width at half maximum, Δλ). Therefore, better color purity is presented. Furthermore, the reflection wavelengths of the obtained cholestric liquid crystal formulation have low temperature dependence (an absolute value of dλ/dT is smaller than 1), thus providing stable display quality.

The liquid crystal composition of the invention can also be mixed with polymerizable monomers to form a homogeneous solution. The monomers are polymerized by heat or light, and as the polymerization progresses, the solubility of the liquid crystal decreases, resulting in phase separation. As a result, liquid crystal droplets formed by the phase separation are evenly dispersed in the polymer, forming the so-called "polymer dispersed cholestric liquid crystal (PDChLC)".

In summary, the chiral compound of the invention provides at least the following.

1. The chiral compound has high helical twisting power.

2. The chiral compound has good solubility in a liquid crystal formulation and is colorless.

3. A cholestric liquid crystal composition containing the chiral compound has high color purity.

4. The chiral compound has stable temperature dependence (an absolute value of dλ/dT is smaller than 1).

The chiral compound of the invention can be used to provide an optical writing cholestric liquid crystal display having high color purity and stable display quality for a wide variety of applications such as electronic labels, electronic books, smart cards, flat panel displays, billboards, hand-writing computers, or the like.

The liquid crystal composition of the invention can also be used in different kinds of displays, such as twisting nematic (TN) displays, super twisting nematic (STN) displays, color super twisting nematic (CSTN) displays, and thin film transistor (TFT) displays. Moreover, the liquid crystal composition can also be used in manufacturing for reflective polarizers, cholestric reflective polarizers, reflectors, optical compensation films, retardation films, color filters, photochromic coatings, liquid crystal dyes, or the like.

Comparative Example 1

Chiral Compound with Two Photosensitive Groups 1

4-Methoxycinnamic acid (10.7 g, 60 mmol) was added into a two-necked bottle with a reflux condenser settled thereon. SOCl$_2$ was dropped into the bottle through a feeding tube, and stirred under a temperature of 50° C. for about 3 hours. After that, the extra SOCl$_2$ was removed by a vacuum pump to yield a light yellow liquid. Meanwhile, isomannide (7.3 g, 50 mmol) was dissolved in pyridine (20 ml) and dichoromethane (50 ml), wherein the above liquid was added slowly thereto, by a feeding tube and the mixture was stirred under room temperature for 20 hours. After completion of the reaction, the mixture was extracted with aqueous HCl and CH$_2$Cl$_2$, and the organic extract was concentrated to obtain a light yellow oil. The oil was recrystallized by methanol to obtain a white solid with a yield of 28.7% (6.7 g, 14.4 mmol). The chiral compound had an HTP of 45 μm$^{-1}$.

Comparative Example 2

Chiral Compound with Two Photosensitive Groups 2

The same synthesis as that in Comparative Example 1 was repeated, except that the isomannide was replaced by isosorbide. The obtained product was in a white solid form, and the chiral compound had an HTP of 45 μm$^{-1}$.

Example 1

4-Methoxycinnamic acid (10.7 g, 60 mmol) was added into a two-necked bottle with a reflux condenser settled thereon. SOCl$_2$ was dropped into the bottle through a feeding tube, and stirred under a temperature of 50° C. for about 3 hours. After that, the extra SOCl$_2$ was removed by a vacuum pump to yield a light yellow liquid. Meanwhile, isomannide (7.3 g, 50 mmol) was dissolved in pyridine (20 ml) and dichloromethane (50 ml), wherein the liquid described above was added slowly thereto through a feeding tube and the mixture was stirred in an ice bath for 4 hours. After completion of the reaction, the mixture was extracted with aqueous HCl and CH$_2$Cl$_2$, and the organic extract was concentrated to obtain a light yellow oil. The oil was recrystallized by methanol to obtain undesirable byproducts. After removing the byproducts, the product was purified by column chromatography, giving a yield of 33.3% (5.1 g, 16.7 mmol).

-continued

-continued (3-(4-Methoxy-phenyl)-acrylic acid 6-hydroxy-hexahydro-furo[3,2-b]furan-3-yl ester (3.8 g, 15 mmol) was added into a two-necked bottle with a reflux condenser settled thereon. $SOCl_2$ was dropped into the bottle through a feeding tube, and stirred under a temperature of 50° C. for about 3 hours. After that, the extra $SOCl_2$ was removed by a vacuum pump to yield a white solid. Meanwhile, the white solid (1.5 g, 5 mmol) described above was dissolved in pyridine (50 ml) and dichoromethane (50 ml), wherein the liquid described above was added slowly thereto through a feeding tube and the mixture was stirred. Then, a small amount of 4-dimethylaminopyridine was added to the mixture, and the reaction mixture was heated to 80° C. for 20 hours. After completion of the reaction, the mixture was extracted with aqueous HCl and ethyl acetate, and the organic extract was concentrated to obtain a light yellow oil. The product was purified by using column chromatography to obtain a white solid with a yield of 21% (0.6 g, 1 mmol). The chiral compound had an HTP of 60 $\mu m^{-1}$.

Example 2

The same synthesis steps as in the Example 1 was repeated, except that isosorbide was replaced by isomannide. The obtained product was in a white solid form and the chiral compound, had an HTP of 33 $\mu m^{-1}$.

Evaluation Result of Illumination 0.15 g of the chiral compound in the Example 1 was placed in 2.94 g of a nematic liquid crystal host BL-087 (Merck, birefringence of 0.24), and was exposed to UV light (365 nm; about 2 $mW/cm^2$). The wavelength of the cholestric liquid crystal was 568 nm before illumination. The wavelength of the cholestric liquid crystal was 782 nm after illumination for 270 seconds. The shift of the wavelength was as high as 214 nm.

Analysis of Color Purity 0.5 g of the chiral molecules of the Comparative Example 1 and the Example 1 were placed into 6.81 g of a nematic liquid crystal host BL-087 (Merck, birefringence was 0.24), respectively, and were exposed to UV light (365 nm; ~2 $mW/cm^2$) for 0-60 seconds. FWHM (Full width at half maximum) of the wavelength ($\Delta\lambda$) was measured, and the results are shown in Table 1 and FIG. 1.

TABLE 1

| λ (nm) (time of light exposing/s) | Δ λ (nm)/liquid crystal host: BL087 | |
|---|---|---|
| | The Comparative Example 1 | The Example 1 |
| 530 (0 s) | 77 | 71 |
| 562 (20 s) | 79 | 76 |
| 586 (30 s) | 84 | 80 |
| 606 (60 s) | 86 | 83 |

Figure 1:
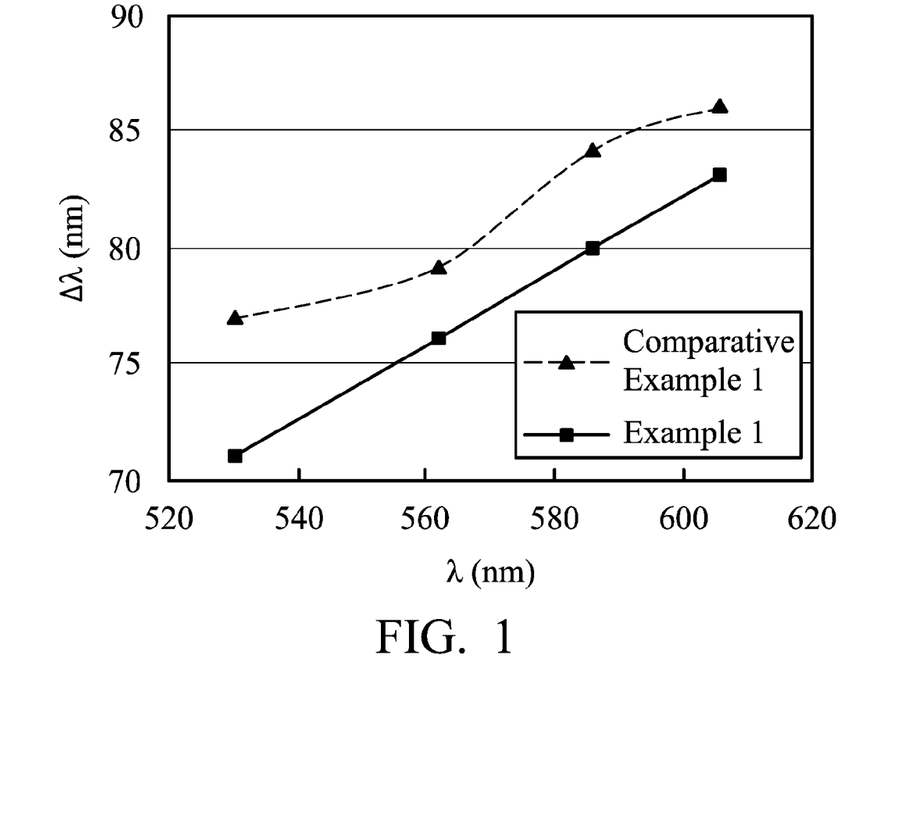
FIG. 1 illustrates the FWHM (Full width at half maximum) of different wavelengths of a liquid crystal formulation which are manufactured in the Example 1 and the Comparative Example 1.

As shown in Table 1 and FIG. 1, the photosensitive cholestric liquid crystal containing the chiral molecules of the Example 1 had smaller Δλ and exhibited better color purity. This was because the molecules of the Example 1 had only one photosensitive group, and therefore the isomerization route from trans to cis was simple. However, the molecules of the Comparative Example 1 had two photosensitive groups, and therefore the isomerization route from (trans, trans) to (cis, cis) required a transitional state of (cis, trans) or (trans, cis), thereby resulting in a larger Δλ.

Figure 2:
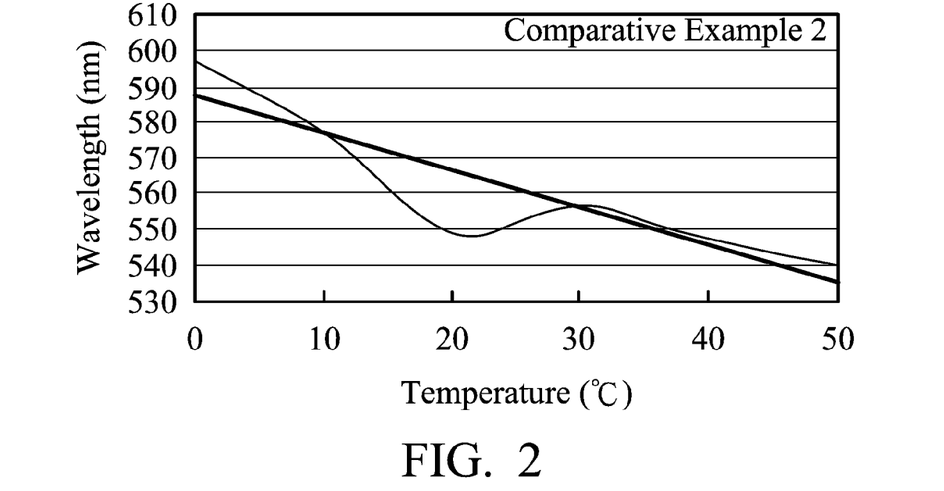
FIG. 2 is a diagram showing the relationship between the temperature and the reflection wavelength of the liquid crystal formulation manufactured in the Comparative Example 2.
Figure 3:
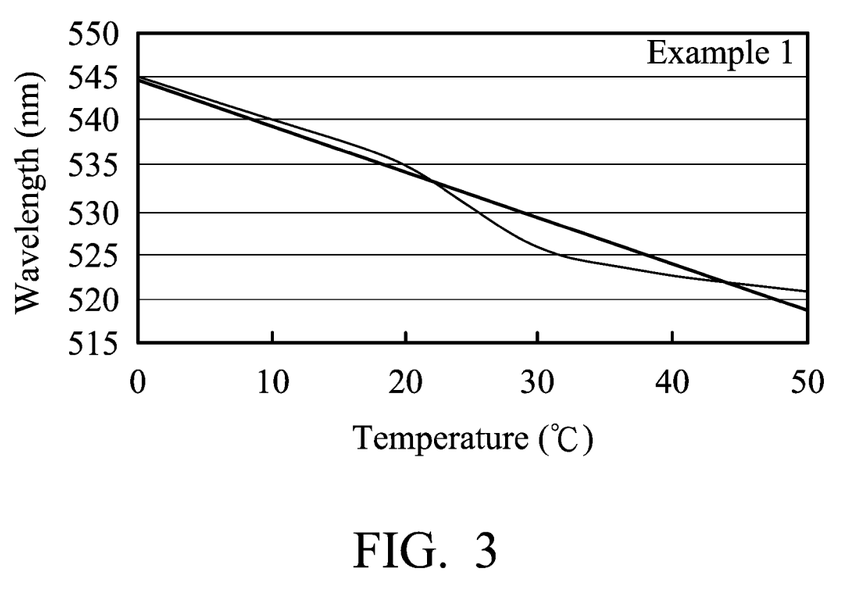
FIG. 3 is a diagram showing the relationship between the temperature and the reflection wavelength of the liquid crystal formulation manufactured in the Example 1.

Analysis of Temperature Dependence 0.4 g of the chiral molecules of the Comparative Example 2 and the Example 1 was added into 4.63 g of a nematic liquid crystal host BL-087 (Merck), respectively. Reflection wavelengths of the obtained cholestric liquid crystal formulation were measured under temperatures of 0-50° C., and the relationships thereof are shown in FIG. 2 and FIG. 3. Linear regression was performed and the slopes (dλ/dT) were −1.05 (Comparative Example 2) and −0.51 (Example 1), respectively. Accordingly, the cholestric liquid crystal formulation of the invention was less temperature sensitive, ensuring display quality.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A chiral compound, having a general formula of formula (I) or (II):

wherein $R_1$ and $R_2$ are independently hydrogen, hydroxyl, halogen, amino, nitro, nitrile, $C_{1-10}$ alkyl, $C_{1-10}$ alkoxyl, aryl, heteroaryl, cycloalkyl, or hetero cycloalkyl.

2. The chiral compound as claimed in claim 1, which has a general formula of formula (I).

3. The chiral compound as claimed in claim 2, wherein $R_1$ and $R_2$ are independently hydrogen, $C_{1-10}$ alkyl, or $C_{1-10}$ alkoxyl.

4. The chiral compound as claimed in claim 1, which has a general formula of formula (II).

5. The chiral compound as claimed in claim 4, wherein $R_1$ and $R_2$ are independently hydrogen, $C_{1-10}$ alkyl, or $C_{1-10}$ alkoxyl.

6. The chiral compound as claimed in claim 1, wherein the chiral compound is in a white solid form.

7. The chiral compound as claimed in claim 1, wherein the helical twisting power of the chiral compound is larger than $30\ \mu m^{-1}$.

8. The chiral compound as claimed in claim 1, which has the following formula:

9. The chiral compound as claimed in claim 1, which has the following formula:

10. A liquid crystal composition, comprising:
  80-99.5 parts by weight of a liquid crystal host; and
  0.5-20 parts by weight of the chiral compound as claimed in claim 1.

11. The liquid crystal composition as claimed in claim 10, wherein an absolute value of a temperature dependence (dλ/dT) for a reflection wavelength of the liquid crystal composition is smaller than 1.

12. The liquid crystal composition as claimed in claim 10, wherein a reflection wavelength of the liquid crystal host is between about 380 and 800 nm.

13. The liquid crystal composition as claimed in claim 10, wherein the liquid crystal host is a nematic liquid crystal.

14. The liquid crystal composition as claimed in claim 13, which is used as a liquid crystal formulation for an optical writing cholesteric liquid crystal display.

15. The liquid crystal composition as claimed in claim 10, wherein the chiral compound has a general formula of formula (I).

16. The liquid crystal composition as claimed in claim 15, wherein $R_1$ and $R_2$ of the chiral compound are independently hydrogen, $C_{1-10}$ alkyl, or $C_{1-10}$ alkoxyl.

17. The liquid crystal composition as claimed in claim 10, wherein the chiral compound has a general formula of formula (II).

18. The liquid crystal composition as claimed in claim 17, wherein $R_1$ and $R_2$ of the chiral compound are independently hydrogen, $C_{1-10}$ alkyl, or $C_{1-10}$ alkoxyl.

19. The liquid crystal composition as claimed in claim 10, wherein the chiral compound has the following formula:

20. The liquid crystal composition as claimed in claim 10, wherein the chiral compound has the following formula:

21. The liquid crystal composition as claimed in claim 10, wherein liquid crystal composition is used in a twisted nematic display, a super twisted nematic display, or a thin film transistor display.

* * * * *